United States Patent [19]

Ehrenpreis et al.

[11] Patent Number: 5,234,949

[45] Date of Patent: Aug. 10, 1993

[54] PARENTERAL SOLUTIONS CONTAINING AMIODARONE IN ACETATE BUFFER SOLUTION

[75] Inventors: Seymour Ehrenpreis, Skokie, Ill.; John C. Somberg, New Rochelle, N.Y.

[73] Assignee: Academic Pharmaceuticals, Inc., Lake Forest, Ill.

[21] Appl. No.: 861,608

[22] Filed: Apr. 1, 1992

[51] Int. Cl.$^5$ ...................... A61K 31/34; A61K 31/19
[52] U.S. Cl. ..................................... 514/469; 514/557
[58] Field of Search .............................. 514/469, 557

[56] References Cited

U.S. PATENT DOCUMENTS 3,248,401  4/1966  Tondeur et al. ............... 260/346.2
4,791,137  12/1988  Descamps ......................... 514/469

OTHER PUBLICATIONS

Escoubet, et al., Am. J. Cardiol., 1985, 55: 696–702.
Mostow et al., Circulation, 1986, 73: 1231–8.
Morady et al., Am. J. Cardiol., 1983, 51: 156–9.
Kadish, et al., Progress in Cardiovascular Diseases, 1989, 31 4: 281–294.
Torres-Arault et al., J. Electrocardiology, 1984, 17 (2): 145–152.
Gough et al., J. Cardiovascular Pharmacology, 1982, 4: 375–380.
Kosinzki, et al., Am. J. Cardiol., 1984 4: 565–70.
Remme et al., Am. Heart J., 1992, 122: 96–103.
Bopp et al., J. Cardio. Pharmacol., 1985 7: 286–289.
Physicians' Desk Reference, 1992, p. 2446.
Cnial Progress in Electrophysiology and Pacing, 1986 4 5: 433.
Remington's Pharmaceutical Sciences, 17th Ed., 1985, pp. 1521–1523.

Primary Examiner—Frederick E. Waddell
Assistant Examiner—Gregory Hook
Attorney, Agent, or Firm—Allegretti & Witcoff, Ltd.

[57] ABSTRACT

Disclosed herein are parenteral solutions containing 3-diethylaminoethoxybenzoyl-benzofurans, such as amiodarone, in acetate buffer useful in the treatment of arrhythmias.

2 Claims, 1 Drawing Sheet

PARENTERAL SOLUTIONS CONTAINING AMIODARONE IN ACETATE BUFFER SOLUTION

BACKGROUND OF THE INVENTION

The present invention relates to novel parenteral solutions containing 3-diethylaminoethoxybenzoylbenzofurans having the following structural formula:

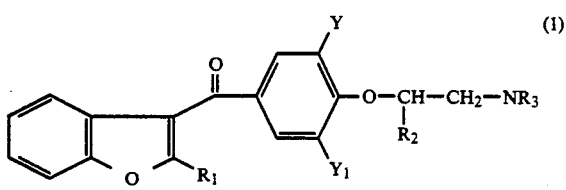

wherein $R_1$ is alkyl, $R_2$ is hydrogen or methyl, $NR_3$ is dimethylamino, diethylamino, dipropylamino, piperidino, pyrrolidino or morpholino, and Y and $Y_1$ are hydrogen, iodo- or bromo-. More particularly, the present invention relates to a parenteral solution suitable for intravenous administration containing as active ingredient 2-n-butyl-3-(3,5-diiodo-4-$\beta$-N-diethylaminoethoxybenzoyl) benzofuran (hereinafter amiodarone).

Amiodarone has been approved in an oral tablet form (CORDARONE®) for the treatment of life-threatening ventricular tachyarrhythmias in the United States since 1985. This drug is useful not only in treating these arrhythmias but also in treating less severe ventricular arrhythmias and many supraventricular arrhythmias including atrial fibrillation and reentrant tachyarrhythmias involving accessory pathways.

To treat arrhythmias, the compound may be administered in oral dosage forms such as in the form of a 200 mg tablet, or it may be administered in the form of an intravenous solution. Please see, for example, Escoubet, B. et al., "Suppression of Arrhythmias Within Hours After Single Oral Dose of Amiodarone and Relation to Plasma and Myocardial Concentrations", *Am. J. Cardiol.*, (1985), 55:696–702, Mostow et al., "Rapid Suppression of Complex Ventricular Arrhythmias With High-Dose Oral Amiodarone", *Circulation*, (1986), 73:1231–8, Morady et al., "Intravenous Amiodarone in the Acute Treatment of Recurrent Symptomatic Ventricular Tachycardia", *Am. J. Cardiol.*, (1983), 51:156–9 and Kadish et al. "The Use of Intravenous Amiodarone in the Acute Therapy of Life-Threatening Tachyarrhythmias". *Progress in Cardiovascular Diseases*, (1989), 31:4, 281–294.

Amiodarone is practically insoluble or slightly soluble in an aqueous solvent. Hence, it is difficult to formulate a dosage form suitable for intravenous administration. To aid the dissolution in water, for example, a surfactant has been suggested. Thus, the prior art intravenous dosage form for this compound termed I.V. Cordarone, comprises amiodarone dissolved in a solvent comprising polysorbate 80 available under the tradename Tween-80, and benzyl alcohol. Prior art intravenous solutions of amiodarone will be designated IV Cordarone herein.

However, the use of this dosage form is highly undesirable because it exhibits deleterious cardiovascular effects attributable to the detergent. For example, Torres-Arrault et al. reported in *Journal of Electrocardiology*, 17 (2), 1984, pp 145–152 that Tween-80 is a potent cardiac depressant and causes hypotension in a dog. See also Gough et al., "Hypotensive Action of Commercial Intravenous Amiodarone and Polysorbate 80 in Dogs", *Journal of Cardiovascular Pharmacology*, (1982), 375–380.

Kosinzki, et al., *Am. J. Cardiol.*, (1984) 4: 565–70 report that intravenous amiodarone (IV Cordarone) can result in significant impairment of left ventricular performance in patients with pre-existing left ventricular dysfunction. After acute intravenous bolus administration, patients with a left ventricular ejection fraction greater than 0.35 experienced improved cardiac performance due to both acute and chronic peripheral vasodilation. However, patients with a lower ejection fraction developed a 20% decrease in cardiac index and clinically significant elevation of right heart pressures after acute bolus administration.

Remme et al., *Am. Heart J.*, (1991) 122: 96–103 report that intravenous amiodarone caused a 15% reduction in blood pressure and an 18% increase in heart rate, and a progressive reduction in contractility ($V_{max}$) with a rise in left ventricular and diastolic pressure.

Bopp et al., *J. Cardio. Pharmacol.*, (1985) 7: 286–289 report that IV cordarone caused a decrease in the ejection fraction, an increase in pulmonary wedge pressure and a 15% decrease in dP/dt, and a 12% decrease in left ventricular work.

Each of the above three references discuss the effects of intravenous amiodarone (IV Cordarone), i.e., amiodarone solubilized for intravenous administration using polysorbate 80 and benzyl alcohol.

The present invention provides a parenteral solution of amiodarone which overcomes these disadvantages.

DESCRIPTION OF THE PRIOR ART

Prior art is replete with the preparation and use of amiodarone. For example, U.S. Pat. No. 3,248,401 issued Apr. 26, 1966 describes the preparation of 3-diethylaminoethoxybenzoyl benzofurans the disclosure of which is incorporated herein by reference.

*Physicians' Desk Reference*, 1992, page 2446 under tradename Cordarone®, provides the prescribing information relating to the oral form of this important product.

The Torres-Arrault, Taska and Gough articles described above set forth the hypotensive effects following intravenous administration of IV Cordarone (amiodarone in Tween-80).

The article "Intravenous Amiodarone", *Clinical Progress in Electrophysiology and Pacing*, (1986), 4:5, page 433 concludes that "Amiodarone, when administered intravenously, appears to have a rapid onset of action causing profound hemodynamic and electrophysiological effect.".

SUMMARY OF THE INVENTION

The present invention relates to parenteral solutions comprising as an active ingredient a 3-diethylaminoethoxybenzoyl-benzofuran with the following structural formula:

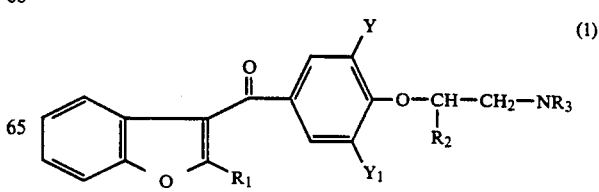

wherein $R_1$ is alkyl, $R_2$ is hydrogen or methyl, $NR_3$ is dimethylamino, diethylamino, dipropylamino, piperidino, pyrrolidino or morpholino and Y and $Y_1$ are identical and represent hydrogen, iodo or bromo. More particularly, the present invention relates to a parenteral solution suitable for intravenous administration containing as an active ingredient an effective anti-arrhythmic amount of 2-n-butyl-3-(3,5-diiodo-4-$\beta$-N-diethylaminoethoxybenzoyl) benzofuran (amiodarone) in a sterile solvent comprising an acetate buffer having a Ph from about 3.5-3.8, i.e., an amiodarone-acetate buffer solution.

The present invention also includes within its scope a method for producing such a solution.

DETAILED DESCRIPTION OF THE INVENTION

Figure 1A:
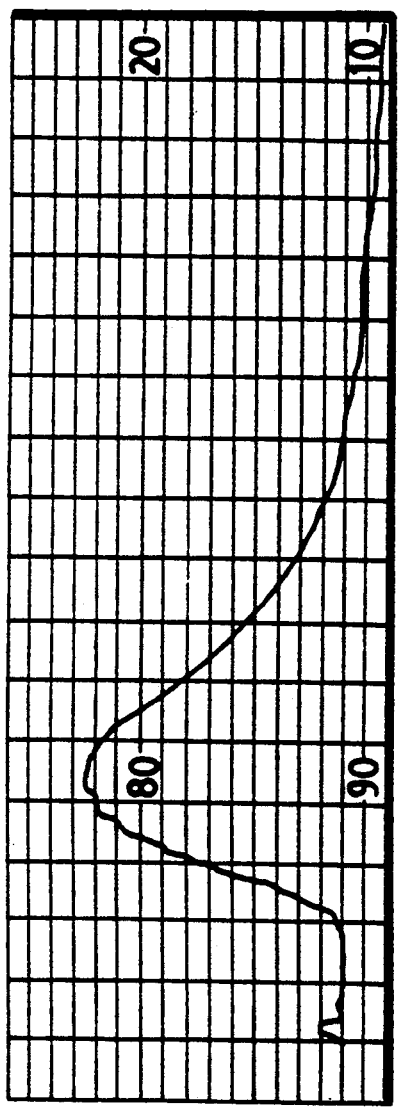
FIG. 1A is a print-out showing the results of high performance liquid chromatography (HPLC) performed on a sample of amiodarone in acetate buffer. The large peak is the amiodarone peak.

According to the present invention, there is provided parenteral solutions containing as an active ingredient 3-diethylaminoethoxybenzoyl benzofuran having the following structural formula:

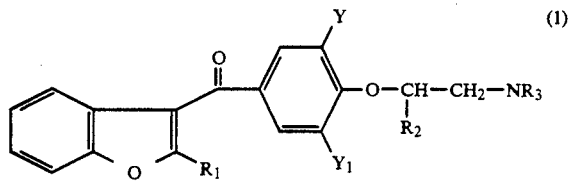

wherein $R_1$ is alkyl of 1-6 carbon atoms, $R_2$ is hydrogen or methyl and $R_3$ is dimethylamino, diethylamino, dipropylamino, piperidino, pyrrolidino or morpholino, and $Y_1$ and $Y_2$ are hydrogen, iodo or bromo. In particular, the present invention relates to a parenteral solution suitable for intravenous administration comprising as an active ingredient an effective anti-arrhythmic amount of a selected substituted benzofuran, i.e., amiodarone in a vehicle which is described more fully below.

In a typical practice of the present invention, amiodarone Hcl, which may be purified and crystalline, is dissolved in a buffer system comprising a weak acid and a salt of the weak acid, and more particularly a combination of acetic acid and sodium acetate having a Ph below 4 and in particular at a range of about 3.5 to 3.8 and a molar concentration of about 0.05 to about 0.1M. An effective anti-arrhythmic amount of amiodarone, e.g., about 25-75 mg/ml, is mixed together with the buffer and heated to a temperature not to exceed about 75° C., i.e., from about 60° to 75° C. and preferably from about 60° to 65° C. until solution is complete. Thereafter, the resulting solution is cooled to room temperature, sterilized by known means, e.g., ultrafiltration or ethylene oxide treatment, and packaged into vials suitable for dispensing as parenteral products.

The preparation thus obtained was found, quite surprisingly, to remain in solution, which of course is an important attribute for a product for intravenous administration. In fact, the product shows remarkable stability when stored at room temperature over a 4 month period without the formation of turbidity or precipitate.

The solution thus formulated is indicated for the treatment of life-threatening, sustained ventricular tachycardia or fibrillation without the fear of the undesirable side effects observed with the administration of a solution of amiodarone in Tween-80. As with any potent drug, the dosage must be individualized by the treating clinician.

In order to further illustrate the practices of the invention, the following examples are included.

EXAMPLE 1

Solubilization of Amiodarone in An Aqueous Solution

The vehicle for dissolving amiodarone consists of about 0.05 to 0.1M acetate buffer with the Ph in the range of about 3.5 to 3.8. As an example, to make a 50 mg/ml amiodarone solution, one ml of the buffer is added to 50 mg of the compound in a vial and the preparation is mixed using a mixer such as a Vortex mixer. Next the preparation is heated in a water bath such that the contents of the vial (buffer and amiodarone) does not exceed about 75° C., i.e., from about 60° to 75° C. and preferably from about 60° to 65° C. The preparation is then cooled to room temperature. Amiodarone dissolved in the new vehicle remains in solution at room temperature in concentrations of about 25 to 50 mg/ml for an extended period of time. Amiodarone which initially went into solution when heated in a 0.2M acetate buffer in the same pH range, formed a gel after cooling. On the other hand, a buffer (0.1M acetate) to which physiologic saline solution was added (0.9% NaCl) formed a precipitate when cooled to room temperature. In phthalate buffer (0.1M, pH 3.5 to 3.8) a precipitate formed when the heated solution cooled. Heating in phosphate buffer (0.1M, pH 3.5 to 3.8) dissolved the compound, while upon cooling gel formation occurred at all pH's.

EXAMPLE 2

Characteristics and Attributes of the Preparation of Example 1

The most important characteristic of the amiodarone-acetate buffer preparation is that amiodarone remains in solution. To analyze solution stability, solutions of about 25 to 75 mg/ml, preferably about 25 mg/ml, amiodarone were prepared as described in Example 1 and maintained at room temperature. The solutions were examined periodically over a period of four months following preparation; the solutions remained perfectly clear, i.e., no sign of turbidity or precipitate. However, at a pH above 4.0 a gel formed at room temperature.

Figure 1B:
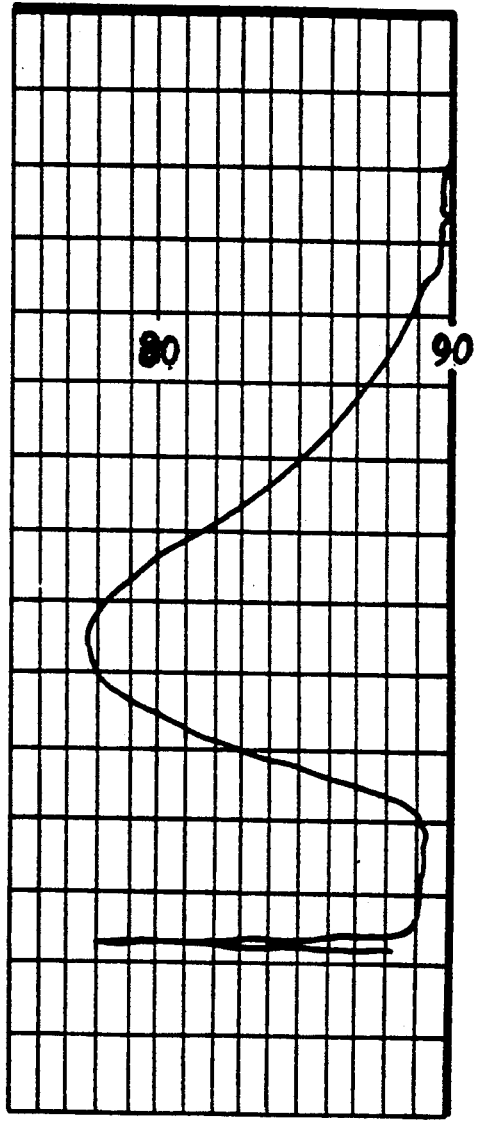
FIG. 1B is a print-out showing the results of high performance liquid chromatography (HPLC) performed on a sample of IV Cordarone (amiodarone in polysorbate 80). The narrow spike is the polysorbate 80 peak and the large peak is the amiodarone peak.

Evaluation of the amiodarone-acetate buffer solution developed through this process demonstrates that the physical and chemical properties of amiodarone remain unchanged as determined by HPLC. As shown in FIGS. 1A and 1B, the peak of amiodarone dissolved in polysorbate 80 (Tween-80) (FIG. 1B) is identical to the peak observed for the amiodarone HCl in the acetate buffer of the present invention (FIG. 1B). The tween-80 peak of the former preparation is clearly visible, this being the only difference between the two HPLC tracings.

EXAMPLE 3

Biologic Activity: Anti-Arrhythmic Activity

The activity of amiodarone that is relevant here is the drug's anti-arrhythmic action. A standard method of determining this activity is to ligate the left anterior descending coronary artery of the rat and record the arrhythmic activity with and without anti-arrhythmic drug pretreatment. The effects of increasing doses of the of the IV Cordarone was evaluated following coronary occlusions with the administration of the drug intravenously 15 minutes before coronary occlusion. While ventricular premature contraction (VPC) frequency was only suppressed at the highest doses, the frequency and severity of the most serious arrhythmias, ventricular tachycardia (VT) and ventricular fibrillation (VF) are suppressed in a dose dependent fashion (Table 1). Amiodarone prepared according to Example 1 studied at the same range of doses caused a similar decrease in VPC frequency, as well as VT and VF incidence (Table 2). This dose-dependent suppression of arrhythmias seen with amiodarone is significantly different than that seen with the saline control group. The amiodarone-acetate buffer preparation (maintained at room temperature for two months) was equally effective as that of a freshly prepared solution. Thus the preparation of the present invention demonstrated long term biologic stability.

TABLE 1

Antiarrhythmic Effects Following Coronary Occlusion (Rat) With IV Cordarone

|  | VPC/30 min | VT Events | VF Events |
|---|---|---|---|
| Saline (no amiodarone) | 226 ± 96 | 17 ± 9 | 5 ± 5 |
| 0.5 mg/kg (n = 5) | 222 ± 30 | 17 ± 5 | 2 ± 1 |
| 1 mg/kg (n = 5) | 145 ± 29 | 15 ± 30 | 0.6 ± 2 |
| 3 mg/kg (n = 5) | 82 ± 45 | 5 ± 6 | 0.3 ± 0 |
| 5.0 mg/kg (N = 5) | 208 ± 121 | 4 ± 5 | 0 |
| 10.0 mg/kg (N = 5) | 129 ± 135 | 3 ± 5 | 0 |
| 20.0 mg/kg (N = 5) | 200 ± 100 | 1 ± 3 | 0 |

TABLE 2

Antiarrhythmic Effects Following Coronary Occlusion (Rat) With Amiodarone-Acetate Buffer Preparation of Example 1

|  | VPC/30 min | VT Events | VF Events |
|---|---|---|---|
| 5.0 mg/kg (N = 6) | 97 ± 66 | 5 ± 4 | 0 |
| 10.0 mg/kg (N = 5) | 111 ± 58 | 3 ± 3 | 0 |
| 20.0 mg/kg (N = 5) | 38 ± 14 | 0 | 0 |

EXAMPLE 4

Biologic Activity: Additional Cardiovascular Attributes of the New Preparation

Effects on Contractility

The new preparation according to the present invention is endowed with certain unique cardiovascular properties. Thus, the new preparation shows considerably less depressant cardiac contractile effects than the IV Cordarone solution. Studies on cardiac contractility were carried out as follows:

Groups of 5 or 6 rats, 450–550 grams were used. Rats were anesthetized with pentobarbital, 60 mg/kg IP. When the rats were anesthetized, the heart was exposed. The heart was suspended in a pericardial cradle and a Walton-Brody strain gauge was sutured to the left ventricle. The strain gauge arch was sutured into place in such a way as to stretch the left ventricle approximately 50%.

The effects of the amiodarone preparations were determined in two ways: fixed dosage and increasing dosage.

Effects on Contractility: Fixed Dosage Method

The protocol for the fixed dosage method was as follows: rats received one fixed dosage (6 rats per group) of amiodarone-acetate buffer solution or IV Cordarone. Measurements were made with the Walton-Brody strain gauge and compared between the groups receiving amiodarone-acetate buffer solution and IV Cordarone. This model has previously been shown to be reasonably valid as an indicator of left ventricular depression induced by various negative inotropic agents, including antiarrhythmics.

The results of this study are shown in Table 3A. These results indicate that the degree of change (depression) of cardiac contractility was significantly less for amiodarone-acetate buffer preparation than IV Cordarone at all doses.

TABLE 3A

Comparative Effects of Amiodarone-Acetate Buffer And IV Cordarone on Cardiac Contractility: Fixed Dosage

| | % Change in Cardiac Contractility[1] (mean ± standard deviation) | | |
|---|---|---|---|
| | 5 mg/kg | 10 mg/kg | 20 mg/kg |
| IV Cordarone n = 6 | −25 ± 12 | −29 ± 8 | −36 ± 19 |
| Amiodarone-Acetate Buffer Solution n = 6 | 0.8 ± 11 | 3 ± 10 | −17 ± 11 |

[1]Percentage change from the baseline (before drug) determined using a Walton Brody Strain Guage Arch sutured to the left ventricle. Negative numbers represent a decrease in contractility and positive numbers an increase.

Effect on Contractility: Increasing Dosage

The percentage change from three independent baseline determinations was measured from the strain gauge excursion at 3 incremental doses of amiodarone. Measurements were made at baseline and at 15 minutes following injection. Another 15 minutes was allowed before the next higher dose was injected.

The results obtained are shown in Table 3B below. These results demonstrate that the new amiodarone preparation causes significantly less depression in cardiac contractility than IV Cordarone. This is a major difference between the preparations which may enable amiodarone in the new vehicle to be administered to sicker patients having more impaired left ventricular function.

TABLE 3B

Comparative Effects of Amiodarone-Acetate Buffer Solution and IV Cordarone on Cardiac Contractility: Increasing Dosage

| | % Change in Cardiac Contractility (mean ± standard deviation) | | |
|---|---|---|---|
| | 5 mg/kg | 10 mg/kg | 20 mg/kg |
| IV Cordarone n = 5 | −34 ± 12 | −38 ± 7.5 | −48 ± 7.4 |
| Amiodarone-acetate buffer solution n = 5 | −15 ± 7.7 | −14 ± 10 | −16 ± 10 |

Effects on Blood Pressure

The effects of an amiodarone-acetate buffer solution prepared according to the invention were contrasted with IV Cordarone in terms of hypotensive action. Amiodarone-acetate buffer solution causes a slight change in blood pressure unlike the IV Cordarone which caused a profound lowering of arterial blood pressure following intravenous administration. The protocol for this study is as follows.

Amiodarone in acetate buffer solution, was compared to IV Cordarone using rats anesthetized with pentobarbital (60 mg/kg). A cannula was inserted into the left carotid artery and attached to a calibrated Stathem P-23 DB Transducer. Blood pressure was recorded from the transducer.

The systolic and diastolic blood pressures are determined before and after the administration of increasing doses of the amiodarone-acetate buffer preparation, or IV Cordarone. Following administration of the investigational agent and observation of change in blood pressure, 15 minutes was allowed for baseline blood pressure to be achieved again, following which increasing doses of the agent are administered.

| Total Number of Animals Used: | 8 Rats |
|---|---|
| Weight: | 450–550 grams each |
| Amiodarone-acetate buffer solution: | 4 |
| IV Cordarone: | 4 | the changes in blood pressure found with the different preparations are listed in Table 4.

TABLE 4

The Comparative Effects of IV Cordarone and Amiodarone-Acetate Buffer Solution on Systolic and Diastolic Blood Pressure (mean ± S.D.)

| IV Cordarone | 3.0 mg/kg | 5.0 mg/kg | 10 mg/kg | 20 mg/kg |
|---|---|---|---|---|
| Change in Systolic BP (% change from baseline) | −20 ± 8 | −21 ± 12 | −36 ± 11 | −33 ± 7 |
| Change in Diastolic BP (% change from baseline) | −11 ± 8 | −19 ± 5 | −20 ± 9 | −31 ± 13 |
| Amiodarone-acetate buffer solution | | | | |
| Change in Systolic BP (% change from baseline) | 0 ± 3 | −3 ± 8 | −8 ± 15 | −13 ± 12 |
| Change of Diastolic BP | 8 ± 10 | −5 ± 9 | −15 ± 17 | −10 ± 7 |

From the above data, it can be summarized that IV Cordarone causes greater depression in blood pressure during IV dosing of the amiodarone acetate buffer solution prepared in Example 1. This difference is directly attributable to the presence of polysorbate 80/benzyl alcohol in the IV Cordarone preparation.

The Electrophysiologic Effect of Amiodarone

Amiodarone in acetate buffer solution prepared according to the invention was compared to IV Cordarone. In this model, animals were anesthetized with pentobarbital (60 mg/kg) intraperitoneally (i.p.). The animal was connected to an electrocardiogram (ECG) and the ECG obtained at baseline and then at 5 minute intervals throughout the experimental period. Following administration of drug, an ECG was recorded every 5 minutes for the ensuing 30 minutes. The heart rate, PR, QRS and QT intervals were determined from the surface ECG recorded at 50 mm/sec. A continuous recording of the ECG is stored on magnetic tape.

| Total Number of Animals Used: | 30 Rats (Sprague Dawley) |
|---|---|
| Weight: | 450–550 grams each |
| Amiodarone-acetate buffer solution: | 15 |
| (5 at each dosage increment) | |
| IV Cordarone: | 15 |
| (5 at each dosage increment) | |

Results: Neither IV Cordarone nor the amiodarone in acetate buffer solution caused significant dose dependent alterations in either the PR, QRS or QT intervals in this rat model.

Also, following administration of increasing doses of amiodarone-acetate buffer solution or IV Cordarone, PR, QRS and QT intervals were observed for 30 minutes. No significant differences in these parameters was noted between amiodarone-acetate buffer solution and IV Cordarone. There was however, a significant difference in terms of reduction in heart rate.

Toxicity of Amiodarone in Acetate Buffer Solution Compared with IV Cordarone Toxicity of amiodarone in acetate buffer was compared with IV Cordarone. To determine the intravenous toxicity of the amiodarone-acetate buffer solution, a rat model was employed with continuous EKG monitoring. The amiodarone-acetate buffer solution was administered intravenously in doses of 10 mg/kg at 3 minute intervals to the point of death. The same procedure was carried out with IV Cordarone. Whereas the average dose of the amiodarone-acetate buffer solution to produce death was 50 mg/kg, the average for IV Cordarone was 35 mg/kg (Table 5). The enhanced safety of the new preparation is a significant property. One of 6 animals died with amiodarone-acetate buffer solution when 50% of those receiving an equal amount of the IV Cordarone were dead due to the heart stopping (asystole) or ventricular fibrillation. (See Table 5 below.) At a dose which was lethal to all rats in the IV Cordarone group only 50% of those receiving the amiodarone-acetate buffer solution died (Table 5).

TABLE 5

Toxicity (Lethality) of Amiodarone in Acetate Buffer Preparation Compared with IV Cordarone Determined By Cumulative Dosing in the Rat

| Dose (mg/kg) | IV Cordarone number of deaths (%) | Amiodarone-acetate buffer number of deaths (%) |
|---|---|---|
| 10 | 0 (0) | 0 (0) |
| 20 | 0 (0) | 0 (0) |
| 30 | 1 (17) | 0 (0) |
| 40 | 4 (66) | 1 (17) |
| 50 | 6 (100) | 3 (50) |
| 60 | | 5 (83) |
| 70 | | 6 (100) |

EXAMPLE 6

Preparation of An Intravenous Dosage Form

A solution prepared according to Example 1 is sterilized, sealed using a sterile ultrafiltration membrane, and packaged into a sterile glass ampule and sealed under aseptic conditions giving a dosage form suitable for intravenous injection and containing about 25-50 mg/ml of amiodarone.

What is claimed is:

1. A solution suitable for parenteral administration which comprises as an active ingredient about 25 to 50 mg/ml of amiodarone in about 0.05 to 0.1M acetate buffer solution having a pH of about 3.5 to 3.8.

2. A method for the treatment of a patient suffering from arrhythmia which comprises the intravenous administration of a solution according to claim 1.

* * * * *